United States Patent
Govari et al.

(10) Patent No.: US 11,107,213 B2
(45) Date of Patent: Aug. 31, 2021

(54) CORRECTING MEDICAL SCANS

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 199 days.

(21) Appl. No.: 16/536,693

(22) Filed: Aug. 9, 2019

(65) Prior Publication Data
US 2020/0211181 A1 Jul. 2, 2020

Related U.S. Application Data

(60) Provisional application No. 62/785,941, filed on Dec. 28, 2018.

(51) Int. Cl.
G06T 7/00 (2017.01)
A61B 5/055 (2006.01)
(Continued)

(52) U.S. Cl.
CPC ............ *G06T 7/0012* (2013.01); *A61B 1/233* (2013.01); *A61B 5/055* (2013.01); *A61B 5/066* (2013.01);
(Continued)

(58) Field of Classification Search
CPC ......... G06T 7/0012; G06T 5/50; G06T 15/08; G06T 5/007; G06T 2207/10081;
(Continued)

(56) References Cited

U.S. PATENT DOCUMENTS

| 6,016,333 | A |   | 1/2000 | Kalvin |
| 6,109,270 | A | * | 8/2000 | Mah ..................... A61B 90/11 606/130 |

(Continued)

FOREIGN PATENT DOCUMENTS

| WO | WO2014/139021 | 9/2014 |
| WO | WO2015/101913 | 7/2015 |

OTHER PUBLICATIONS

Higgins, William E. "3D CT-Video Fusion for Image-Guided Bronchoscopy" Computerized Medical Imaging and Graphics. (Year: 2007).*

(Continued)

*Primary Examiner* — Kim Y Vu
*Assistant Examiner* — Molly Delaney
(74) *Attorney, Agent, or Firm* — Todd J. Burns

(57) ABSTRACT

In one embodiment a medical scan correction system includes a medical instrument having a distal end and an image sensor disposed at the distal end, and configured to be inserted into a body-part of a living subject, and a controller to register a medical scan of the body-part with a coordinate frame of the medical instrument, the medical scan including initial tissue-type indications, render a first image including a representation of the body-part and the initial tissue-type indications based on the medical scan, and a representation of the medical instrument, render a second image captured by the image sensor of a portion of the body-part, and responsively to a comparison between an appearance of a tissue in the second image of the portion of the body-part and an initial tissue-type indication of the tissue, update the medical scan to modify the tissue-type indication associated with the tissue.

23 Claims, 12 Drawing Sheets

(51) Int. Cl.
| | |
|---|---|
| *A61B 5/06* | (2006.01) |
| *A61B 6/03* | (2006.01) |
| *A61B 34/10* | (2016.01) |
| *A61B 1/233* | (2006.01) |
| *A61B 17/24* | (2006.01) |
| *G06T 5/50* | (2006.01) |
| *G06T 15/08* | (2011.01) |
| *A61B 6/00* | (2006.01) |
| *G06T 5/00* | (2006.01) |

(52) U.S. Cl.
CPC .............. *A61B 6/032* (2013.01); *A61B 17/24* (2013.01); *A61B 34/10* (2016.02); *G06T 5/50* (2013.01); *G06T 15/08* (2013.01); *A61B 6/501* (2013.01); *A61B 6/5205* (2013.01); *A61B 2034/107* (2016.02); *G06T 5/007* (2013.01); *G06T 2207/10081* (2013.01); *G06T 2207/10088* (2013.01); *G06T 2207/10104* (2013.01); *G06T 2207/30016* (2013.01)

(58) Field of Classification Search
CPC . G06T 2207/10088; G06T 2207/10104; G06T 2207/30016; A61B 34/10; A61B 1/233; A61B 5/055; A61B 5/066; A61B 6/032; A61B 17/24; A61B 2034/107; A61B 6/501; A61B 6/5205; A61B 90/36; A61B 90/37; A61B 2090/364; A61B 34/20; A61B 34/25; A61B 2034/2051; A61B 2034/2072; A61B 6/58; A61B 6/582
See application file for complete search history.

(56) References Cited

U.S. PATENT DOCUMENTS

| | | | |
|---|---|---|---|
| 7,904,145 B2* | 3/2011 | Hashimshony | A61B 5/0091 600/547 |
| 2003/0174872 A1* | 9/2003 | Chalana | G16H 50/70 382/128 |
| 2007/0013710 A1* | 1/2007 | Higgins | G06K 9/00208 345/581 |
| 2007/0100332 A1 | 5/2007 | Paul et al. | |
| 2009/0093806 A1 | 4/2009 | Govari et al. | |
| 2009/0118609 A1 | 5/2009 | Rahn | |
| 2013/0077840 A1 | 3/2013 | Blumfield et al. | |
| 2013/0266198 A1 | 10/2013 | Pereira et al. | |
| 2016/0007842 A1 | 1/2016 | Govari et al. | |
| 2016/0067007 A1* | 3/2016 | Piron | A61B 34/20 705/3 |
| 2017/0035517 A1* | 2/2017 | Geri | G06T 19/20 |
| 2017/0056112 A1 | 3/2017 | Gliner et al. | |
| 2017/0079553 A1 | 3/2017 | Gliner | |
| 2017/0258352 A1* | 9/2017 | Wood | A61B 5/6868 |
| 2017/0312032 A1* | 11/2017 | Amanatullah | G09B 23/30 |

OTHER PUBLICATIONS

European Search Report dated May 15, 2020 from corresponding European Patent Application No. 19217927.3.

* cited by examiner

CORRECTING MEDICAL SCANS

RELATED APPLICATION INFORMATION

The present application claims priority from U.S. Provisional Patent Application No. 62/785,941 of Govari, et al., filed on Dec. 28, 2018, the disclosure of which is hereby incorporated herein by reference.

FIELD OF THE INVENTION

The present invention relates to medical scans, and in particular, but not exclusively, to correcting medical scans.

BACKGROUND

By way of introduction, a medical instrument may be used in brain surgery or sinus dilation among other applications. In sinus dilation, a medical instrument may be inserted via the nasal cavity through various sinus cavities. In brain surgery, instead of opening skull to remove a tumor, a medical tool may be inserted via the nasal cavity and the sinus cavities.

Segmented computed tomography (CT) images may aid navigation of the medical instrument during such a medical procedure. After production of a CT image, the elements of the CT image may typically be segmented automatically. The segmentation normally operates by assigning ranges of Hounsfield Unit values in the CT image to different types of matter, e.g., one range for bone and another for soft tissue. However, there are sometimes errors in the segmentation.

Segmentation and correction of medical scans is known in the art. For example, US Patent Publication 2013/0266198 of Pereira, et al., describes a method that generates attenuation correction maps for the reconstruction of positron emission tomography (PET) using magnetic resonance (MR) images, such as, MR ultra-fast TE (UTE) images, Dixon MR images, as well as MR images obtained using other MR imaging methods.

US Patent Publication 2013/0077840 of Blumfield, et al., describes a method for automated segmentation of human vertebral body images in a CT study. The method was developed to enable automated detection of osteoporosis in CT studies performed for other clinical reasons.

U.S. Pat. No. 6,016,333 to Kalvin describes a system and method to improve the quality of noisy CT images that have been generated by a CT scanner running on low-power. The image noise is reduced by restoring crucial quantitative image information.

SUMMARY

There is provided in accordance with an embodiment of the present disclosure, a medical scan correction system including a medical instrument having a distal end and an image sensor disposed at the distal end, and configured to be inserted into a body-part of a living subject, a position sensor configured to track an instrument position of the medical instrument in the body-part, a display, and a controller configured to register a medical scan of the body-part with a coordinate frame of the medical instrument, the medical scan including a plurality of initial tissue-type indications of the body-part, render to the display, a first image including a representation of the body-part and the plurality of initial tissue-type indications based on the medical scan, and a representation of the medical instrument disposed at the tracked instrument position in the body-part, render to the display, a second image captured at the tracked instrument position by the image sensor of a portion of the body-part, and responsively to a comparison between an appearance of a tissue in the second image of the portion of the body-part and an initial tissue-type indication of the tissue, update the medical scan to modify the tissue-type indication associated with the tissue.

Further in accordance with an embodiment of the present disclosure, the system includes operating controls configured to receive a user input to update the medical scan modifying the tissue-type indication associated with the tissue from the initial tissue-type indication of the tissue.

Still further in accordance with an embodiment of the present disclosure the controller is configured to find the tissue in the medical scan responsively to the tracked instrument position.

Additionally, in accordance with an embodiment of the present disclosure the controller is configured to render to the display, a textual indication of the initial tissue-type indication of the tissue.

Moreover, in accordance with an embodiment of the present disclosure the controller is configured to emphasize the tissue in the first image.

Further in accordance with an embodiment of the present disclosure the plurality of initial tissue-type indications are levels of radiodensity in the medical scan.

Still further in accordance with an embodiment of the present disclosure the controller is configured to update the medical scan to reclassify all tissues of the body-part in the medical scan being initially classified with the initial tissue-type indication of the tissue to the modified tissue-type indication of the tissue.

Additionally, in accordance with an embodiment of the present disclosure the plurality of initial tissue-type indications are levels of radiodensity in the medical scan.

Moreover, in accordance with an embodiment of the present disclosure the controller is configured to update proportionally all the levels of radiodensity in the medical scan responsively to a proportional change between the level of radiodensity of the initial tissue-type indication of the tissue and the level of radiodensity of the modified tissue-type indication of the tissue.

Further in accordance with an embodiment of the present disclosure the controller is configured to update all the levels of radiodensity in the medical scan responsively to a proportional change confirmed by at least two tissue-type indication updates from different ones of the plurality of initial tissue-type indications.

Still further in accordance with an embodiment of the present disclosure the controller is configured to output a warning about the proximity of the medical instrument to the tissue responsively to the tracked instrument position and the tissue being initially classified in the medical scan the initial tissue-type indication of the tissue.

There is also provided in accordance with another embodiment of the present disclosure, a medical scan correction method, including tracking an instrument position of a medical instrument in a body-part of a living subject, the medical instrument having a distal end and an image sensor disposed at the distal end, registering a medical scan of the body-part with a coordinate frame of the medical instrument, the medical scan including a plurality of initial tissue-type indications of the body-part, rendering to a display, a first image including a representation of the body-part and the plurality of initial tissue-type indications based on the medical scan, and a representation of the medical instrument disposed at the tracked instrument position in the body-part, rendering to the display, a second image captured at the tracked instrument position by the image sensor of a portion of the body-part, and responsively to a comparison between an appearance of a tissue in the second image of the portion of the body-part and an initial tissue-type indication of the tissue, updating the medical scan to modify the tissue-type indication associated with the tissue.

Additionally, in accordance with an embodiment of the present disclosure, the method includes receiving a user input to update the medical scan modifying the tissue-type indication associated with the tissue from the initial tissue-type indication of the tissue.

Moreover, in accordance with an embodiment of the present disclosure, the method includes finding the tissue in the medical scan responsively to the tracked instrument position.

Further in accordance with an embodiment of the present disclosure, the method includes rendering to the display, a textual indication of the initial tissue-type indication of the tissue.

Still further in accordance with an embodiment of the present disclosure, the method includes emphasizing the tissue in the first image.

Additionally, in accordance with an embodiment of the present disclosure the plurality of initial tissue-type indications are levels of radiodensity in the medical scan.

Moreover, in accordance with an embodiment of the present disclosure, the method includes updating the medical scan to reclassify all tissues of the body-part in the medical scan being initially classified with the initial tissue-type indication of the tissue to the modified tissue-type indication of the tissue.

Further in accordance with an embodiment of the present disclosure the plurality of initial tissue-type indications are levels of radiodensity in the medical scan.

Still further in accordance with an embodiment of the present disclosure, the method includes updating proportionally all the levels of radiodensity in the medical scan responsively to a proportional change between the level of radiodensity of the initial tissue-type indication of the tissue and the level of radiodensity of the modified tissue-type indication of the tissue.

Additionally, in accordance with an embodiment of the present disclosure, the method includes updating all the levels of radiodensity in the medical scan responsively to a proportional change confirmed by at least two tissue-type indication updates from different ones of the plurality of initial tissue-type indications.

Moreover, in accordance with an embodiment of the present disclosure, the method includes outputting a warning about the proximity of the medical instrument to the tissue responsively to the tracked instrument position and the tissue being initially classified in the medical scan the initial tissue-type indication of the tissue.

There is also provided in accordance with still another embodiment of the present disclosure, a software product, including a non-transient computer-readable medium in which program instructions are stored, which instructions, when read by a central processing unit (CPU), cause the CPU to register a medical scan of a body-part of a living subject with a coordinate frame of a medical instrument configured to be inserted into the body-part, the medical scan including a plurality of initial tissue-type indications of the body-part, render to a display, a first image including a representation of the body-part and the plurality of initial tissue-type indications based on the medical scan, and a representation of the medical instrument disposed at a tracked instrument position of the medical instrument in the body-part, render to the display, a second image of a portion of the body-part captured at the tracked instrument position by an image sensor of the medical instrument, and responsively to a comparison between an appearance of a tissue in the second image of the portion of the body-part and an initial tissue-type indication of the tissue, update the medical scan to modify the tissue-type indication associated with the tissue.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
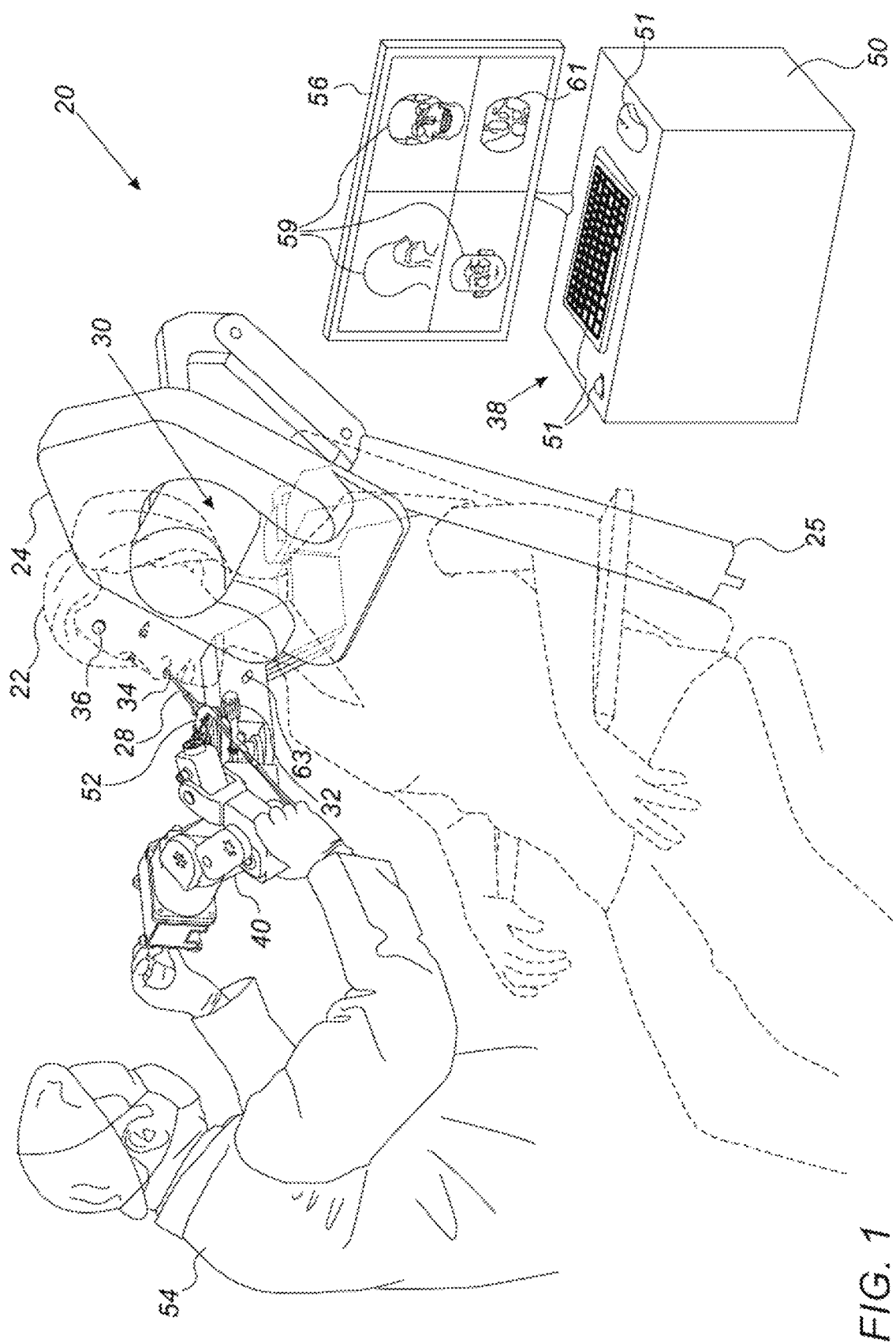
FIG. 1 is a schematic illustration of a medical system, according to an embodiment of the present invention.

As noted earlier, after production of a medical scan such as a CT image, the elements of the medical scan may typically be segmented automatically to assist the viewing physician. The segmentation may operate by assigning Hounsfield Unit values or other suitable measures in the CT images to different types of matter, e.g., bone or soft tissue. However, there are sometimes errors in the segmentation.

Errors in segmentation may be due to errors in the processing of the medical scan or errors in the scanning.

Artifacts in the medical scan may also exist, for example, based on factors related to the scanning such as dental implants resulting in scattering of the incident radiation during scanning and thereby leading to matter, e.g., bone or soft tissue, being classified incorrectly.

An incorrectly segmented medical scan may result in poor or incorrect diagnosis by a physician. In cases where the incorrectly segmented medical scan is used to aid navigation of a medical tool during a medical procedure in a body-part, navigation of the medical instrument may be hampered, and in some situations the medical instrument could damage sensitive tissue. For example, if the physician is warned by a tracking system when the medical instrument is too close to sensitive tissue or is applying too much force to sensitive tissue, the physician may take appropriate caution. However, if the medical scan is incorrectly segmented, appropriate warnings may not occur as the tracking system does not recognize the proximate tissue as being sensitive tissue based on the incorrect medical scan segmentation. In other situations, warnings may be issued regarding proximity to sensitive tissue, when in reality the tissue close to the medical instrument is not sensitive in nature.

Embodiments of the present invention allow a physician to update a medical scan based on a comparison of real-time images captured by an image sensor disposed on a medical instrument inside a body-part with an image of the segmented medical scan of the body-part.

The real-time images captured by the medical instrument and the image of the segmented medical scan are generally displayed together on a display screen. The image of the segmented medical scan indicates different initial tissues-types (e.g., bone, soft-tissue, cartilage, and blood) or matter types (e.g., water or air) using a color-scheme (e.g., grayscale). For example, air may be black or close to black and bone may be white or off-white. A representation of the medical instrument (e.g., using an arrow or schematic of the medical instrument) is superimposed over the image of the segmented medical scan to show the current position of the medical instrument.

The tissue currently included in the real-time images captured by the image sensor of the medical instrument is identified in the medical scan based on a tracked position of the medical instrument. The identified tissue may be emphasized in the image of the medical scan. The tissue may be emphasized using a border, an arrow, a change of format or any other suitable highlighting method. Additionally, or alternatively the tissue-type indication of the identified tissue may be rendered on the display screen as a text message, for example, "bone", "soft-tissue", "Hounsfield unit value 600" etc.

A comparison by the physician of the tissue included in the real-time images with the tissue-type indication (e.g., grayscale value) of the emphasized tissue included in the image of the medical scan may reveal that the initial tissue-type indication of the emphasized tissue is incorrect. The physician may then modify the tissue-type indication of the emphasized tissue using a user interface tool such as a drop-down list or by entering a corrected grayscale value or Hounsfield unit value.

The tissue-type indication of the tissue is then updated in the medical scan and in the image of the medical scan displayed on the display screen.

In some embodiments, the tissue-type indication may be updated for all tissues having the same initial tissue-type indication, as it may be assumed that the same error propagated itself throughout the medical scan. By way of example, if the Hounsfield unit value of the tissue was initially 300 and is now modified to 600, the Hounsfield unit values of all the tissues in the medical scan having an initial Hounsfield unit value of 300 are now modified to 600. In some embodiments, all the initial tissue-type indications in the medical scan may be updated proportionally according to the proportional change in value (e.g., grayscale value or Hounsfield unit value) from the initial tissue-type indication to the modified tissue-type-indication of the emphasized tissue. By way of example, if the Hounsfield unit value of the tissue was initially 300 and is now modified to 600 (i.e., it doubled) all the Hounsfield unit values of the tissues in the medical scan are doubled.

In some embodiments, the comparison of the tissue included in the real-time images with the tissue-type indication (e.g., grayscale value) of the tissue included in the medical scan may be performed in an automatic or semi-automatic fashion. The tissue included in the real-time images may be compared to other tagged tissue images in a library of tissue images to identify the tissue-type of the tissue. Additionally, or alternatively, machine learning techniques may also be used to identify the tissue-type of the tissue. The identified tissue-type may then be compared to the initial tissue-type indication of the tissue included in the medical scan. If the identified tissue-type is different from the initial tissue-type indication, the initial tissue-type indication may be automatically updated to the identified tissue-type or a message may be outputted to the display screen informing the physician that the tissue-type of the tissue viewed in the real-time images does not correlate with the initial tissue-type indication of the tissue included in the medical scan. The physician then has the option to approve or deny updating the initial tissue-type indication according to the identified tissue-type.

Correction of the segmentation of the medical scan may be performed as part of a medical procedure in which the physician is navigating the medical instrument in the body-part and notices that the initial tissue-type indication included in the image of the medical scan does not correspond with the image of the tissue included in the real-time images captured by the image sensor of the medical instrument. The system may draw the physician's attention to the incorrect segmentation when an incorrect warning is issued (e.g., the medical instrument is too close to sensitive tissue when in fact it is adjacent to bone) or a warning is not issued when it should have been (e.g., the medical instrument is too close to the optic nerve and no warning was issued).

In some cases, correction of the segmentation of the medical scan may be initiated by the physician noticing an artifact in the medical scan which the physician wants to investigate further. The physician inserts the medical instrument into the body-part to investigate the actual tissue-type of the tissue associated with the region of the artifact and then proceeds to update the medical scan based on the actual tissue-type identified in the real-time images.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
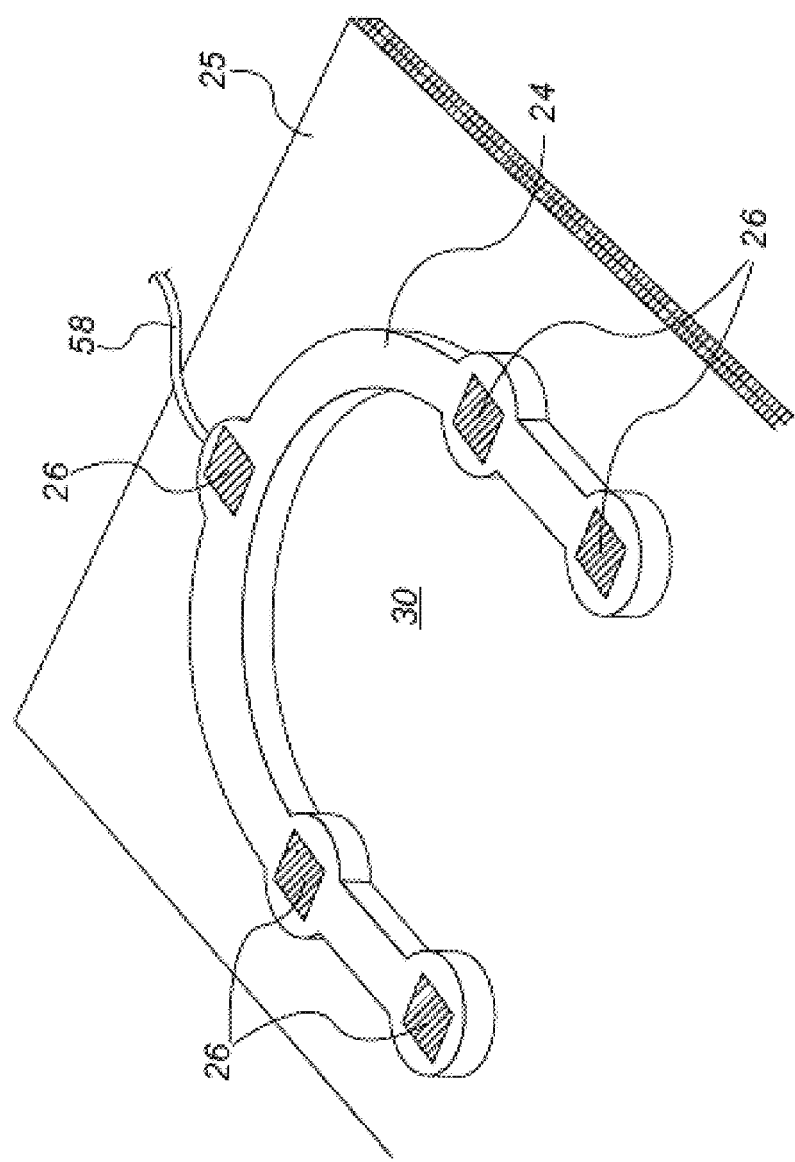
FIG. 2 is a schematic illustration of a magnetic field radiation assembly used in the medical system, according to an embodiment of the present invention.

Turning now to the drawings, reference is now made to FIG. 1, which is a schematic illustration of a medical system 20, and to FIG. 2, which is a schematic illustration of a magnetic field radiation assembly 24 used in the system 20, according to an embodiment of the present invention. The medical system 20 is typically used during an invasive and/or investigative procedure on a nasal sinus or another body part (such as the brain) of a patient 22.

For the procedure, the magnetic field radiation assembly 24 may be positioned behind and/or around the head of the patient 22, for example by fixing the assembly 24 to a chair 25 (or bed) upon which the patient is sitting (or lying). The magnetic field radiation assembly 24 in the pictured example comprises five magnetic field radiators 26, which are fixed in a horseshoe shaped frame, the frame being positioned beneath or around the patient 22 so that the magnetic field radiators 26 surround the head of the patient 22. Alternatively, smaller or larger numbers of radiators 26 may be used, in various different configurations. The magnetic field radiators 26 are configured to radiate alternating magnetic fields at respective frequencies into a region 30, in proximity to the magnetic field radiation assembly 24 and which includes the head of patient 22. The alternating magnetic fields induce signals in a position sensor 32 and a position sensor 36. The position sensor 32 is shown disposed on a medical instrument 28 in order to track a position of the medical instrument 28 in a body-part. By way of example only, the medical instrument 28 may include any one or more of the following, a probe for inserting into the body-part, an endoscope, and/or a surgical tool such as an ENT tool, suction tool, microdebrider, or a shaver.

The medical instrument 28 may be attached to and held by a robotic arm 40, which is configured to manipulate the medical instrument 28. The robotic arm 40 includes a plurality of robotic joints configured to control movement of the robotic arm 40 and manipulate the medical instrument 28. In some embodiments, the medical instrument 28 may be held by the physician 54 or an assistant.

The position sensor 36 is shown disposed on the patient 22 (e.g., on the forehead of the patient 22 or any other suitable body part) in order to track a position of the patient 22 (e.g., to track a position of the head of the patient 22).

Each position sensor 32, 36 typically includes a set of three orthogonal coils, and the signals may be analyzed by a controller 38 to derive the location and orientation of the position sensors 32, 36 with respect to the magnetic field radiation assembly 24. It will be understood that the location and orientation of position sensors 32, 36 may be determined for substantially any positioning of the position sensor within region 30. Although the position sensors 32, 36 are described herein as magnetic position sensors, the positions of the medical instrument 28 and the patient 22 may be computed using any suitable position sensing technology, for example, but not limited to, electrical, ultrasonic, optical, inertial, or any other suitable type known in the art.

As is described in more detail below, position sensor 32 is affixed to the medical instrument 28, and determination of the location and orientation of the position sensor 32 enables the location and orientation of a distal end 34 (or other location) of the medical instrument 28, that may be reversibly inserted into a body-part of the patient 22 (the living subject), to be tracked. When the medical instrument 28 is a rigid medical instrument, the position sensor 32 may generally be disposed on any suitable part of the medical instrument 28 (e.g., the distal end 34 or on a proximal end 52 of the medical instrument 28) and/or on the robotic arm 40 which is holding the medical instrument 28. If the distal end 34 of the medical instrument 28 is flexible, the position sensor 32 is generally disposed on the distal end 34 of the medical instrument 28 in order to accurately track the position of the distal end 34 of the medical instrument 28.

Similarly, determination of the location and orientation of the position sensor 36 enables the location and orientation of the body-part (e.g., head) of the patient 22 to be tracked. The position sensor 36 is shown in FIG. 1 as being disposed on the forehead of the patient 22. The position sensor 36 may be disposed on any other suitable body part of the patient 22 in order to track the position/movement of the patient 22.

A system using magnetic field radiators, such as the magnetic field radiators 26, for tracking an entity inserted into a patient is described in US Patent Publication 2016/0007842, of Govari et al., which is incorporated herein by reference. In addition, the Carto® system produced by Biosense Webster of 33 Technology Drive, Irvine, Calif. 92618 USA, uses a tracking system similar to that described herein for finding the location and orientation of a coil in a region irradiated by magnetic fields.

The robotic arm 40 generally has its own robotic coordinate system. The robotic coordinate system is registered with a magnetic coordinate system of the magnetic field radiators 26 and/or vice-versa. Registration of the robotic coordinate system with the magnetic coordinate system may be performed, for example, by moving the robotic arm 40, or the medical instrument 28 attached to the robotic arm 40, to one or more locations known to the magnetic field radiators 26, for example, to a location on the magnetic field radiation assembly 24 or to the position sensor 36 or to one or more other known locations on the patient 22. Once registration of the robotic coordinate system with the magnetic coordinate system has been performed, locations in the magnetic coordinate system can be translated to the robotic coordinate system in order to manipulate the robotic arm 40 correctly.

Elements of system 20, including radiators 26, may be controlled by the controller 38, which comprises a processing unit communicating with one or more memories. Typically, the elements may be connected by cables to the controller 38, for example, radiators 26 may be connected by a cable 58 to the controller 38. Alternatively, or additionally, the elements may be coupled wirelessly to the controller 38. The controller 38 may be mounted in a console 50, which comprises operating controls 51 that typically include a keypad and/or a pointing device such as a mouse or trackball. The console 50 also connects to other elements of the medical system 20, such as the proximal end 52 of the medical instrument 28. A physician 54 uses the operating controls 51 to interact with the controller 38 while performing the procedure, and the controller 38 may present results produced by system 20 on a display screen 56. In FIG. 1, the display screen 56 is displaying various views 59 of a previous CT scan (or other suitable scan) which may be used as an aid for the physician 54 to guide the medical instrument 28 in the body-part. The display screen 56 also shows an image 61 captured by the medical instrument 28.

In practice, some or all of these functions of the controller 38 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The medical system 20 may optionally include a lens cleaning device 63 configured to clean a lens of an endoscope when an endoscope is included in the medical instrument 28. The lens cleaning device 63 may comprise a water jet sprayer for spraying water on the lens or a wiper to wipe the lens with a suitable material, for example, but not limited to, a piece of gauze. The lens cleaning device 63 may be disposed on the robotic arm 40. Alternatively, or additionally, the lens cleaning device 63 may be implemented as part of the medical instrument 28, for example, with a jet spray, which may be activated when the medical instrument 28 is removed from the body-part.

FIGS. 3A-C, 4, 5 describe the medical instrument 28 as a rigid medical instrument and the position sensor 32 as a movable position sensor which may be fixed to any suitable part of the medical instrument 28 and therefore the location of the position sensor 32 does not initially indicate the distal end 34 of the medical instrument 28 until suitable calibration is performed. In some embodiments, the medical system 20 may be implemented when the position sensor 32 is integrated with the medical instrument 28 and/or the position of the position sensor 32 with respect to the distal end 34 of the medical instrument 28 is already known. In other embodiments, the position sensor 32 may be disposed on the robotic arm 40 and in such a case the location of the position sensor 32 does not initially indicate the distal end 34 of the medical instrument 28 until suitable calibration is performed.

Figure 3:
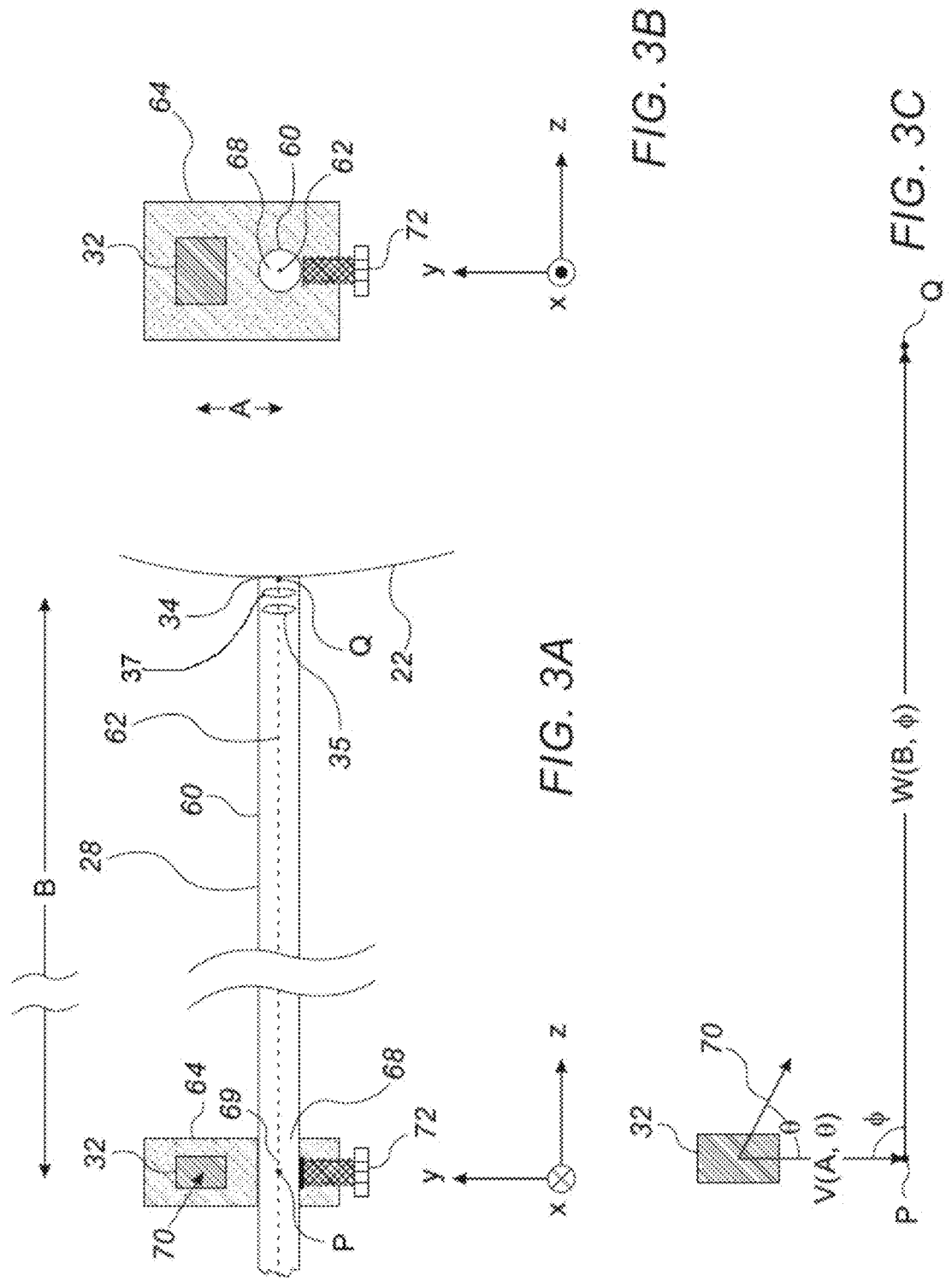
FIG. 3A is a schematic cross-sectional side view of an exemplary medical instrument.
FIG. 3B is a schematic cross-sectional front view of the medical instrument of FIG. 3B.
FIG. 3C is a schematic diagram illustrating vectors related to the medical instrument of FIGS. 3A and 3B, according to an embodiment of the present invention.

FIG. 3A is a schematic cross-sectional side view of the medical instrument 28, FIG. 3B is a schematic cross-sectional front view of the medical instrument 28, and FIG. 3C is a schematic diagram illustrating vectors related to the medical instrument 28, according to an embodiment of the present invention. In the following description of the medical instrument 28, the medical instrument 28 is assumed to comprise a rigid cylinder 60, having a longitudinal symmetry axis 62. In FIGS. 3A and 3B the medical instrument 28 has been drawn on a set of xyz orthogonal axes, with the longitudinal symmetry axis 62 defining the z-axis. For clarity, in FIGS. 3A and 3B the xyz axes of the medical instrument 28 are drawn displaced from the cylinder 60.

The position sensor 32 is fixed to the cylinder 60 by a sensor holder 64, which is typically formed from plastic so as to completely encapsulate the position sensor 32. As explained herein, signals from the position sensor 32, generated in response to the magnetic fields interacting with the position sensor 32, are used to determine a location and an orientation of the position sensor 32. Conducting wires that convey the signals from the position sensor 32 may be connected to the proximal end 52 of the medical instrument 28, and from there to the console 50. The conducting wires are not shown in FIGS. 3A and 3B.

The position sensor 32 is assumed to have a sensor direction 70, typically, but not necessarily, the direction of an internal axis of symmetry of the position sensor 32, and the orientation referred to herein measures the orientation of the sensor direction with respect to a frame of reference defined by the magnetic field radiators 26 (FIG. 2). The sensor direction 70 of the position sensor 32 is shown schematically in FIGS. 3A and 3C as an arrow.

The sensor holder 64 is produced to have a hole 68, which is formed to have a diameter substantially the same as that of cylinder 60, but sufficiently different so that there is a sliding fit between the holder 64 and the cylinder 60. When the holder 64 is produced, a center of the hole 68 is made to be a known distance A from the position sensor 32. A typical value of A is 0.5 cm, but A may be smaller or larger than this value. A series of sensor holders may be constructed, having holes that are dimensioned to medical instruments having different diameters. In addition, by virtue of being comprised in the holder 64, the center of the hole 68 has a known orientation θ with respect to the sensor direction 70. There is thus a known displacement vector (A, θ), herein also termed vector V, from the position sensor 32 to the center of the hole 68, as shown in FIG. 3C.

The hole 68 has an axis of symmetry 69 that is typically orthogonal to the vector V, and which by virtue of being formed when the holder 64 is produced, has a known direction φ with respect to the vector V (FIG. 3C).

As is also described below, in operating the system 20, the hole 68 of the sensor holder 64 is slid onto cylinder 60, and the holder 64 is fixed to the cylinder 60 when the holder 64 is close to the proximal end 52. It will be understood that in sliding the cylinder 60 within the hole 68, the axes 69 and 62 are coincident, and also coincide with direction φ. The holder 64 comprises a setscrew 72, having a head, which may be grasped by the physician 54 (FIG. 1). Using the head, the physician 54 is able to hand-tighten the setscrew to fix the holder 64 at a desired position along the cylinder 60. The distance from the center of the position sensor 32 to the distal end 34 is assumed to be a distance B. Unlike distance A, distance B is not known when sensor holder 64 is fixed to cylinder 60, but as is described below in operation of system 20, the controller 38 is able to calculate distance B.

FIG. 3A also shows a force sensor 35 disposed on, or embedded in, the medical instrument 28. The force sensor 35 is configured to provide a signal which is indicative of a force applied by the medical instrument 28 on the body-part. More than one force sensor 35 may be disposed at different lateral positions along the medical instrument 28 to provide force readings at different locations on the medical instrument 28. U.S. Patent Application Publications 2007/0100332 and 2009/0093806, whose disclosures are incorporated herein by reference, describe methods of sensing contact pressure between the distal tip of a catheter and tissue in a body cavity using a force sensor embedded in the catheter. In addition, the Carto® SmartTouch™ system produced by Biosense Webster of 33 Technology Drive, Irvine, Calif. 92618 USA, includes force sensors appropriate for the medical system 20.

The medical instrument 28 also includes an image sensor 37 disposed at the distal end 34. The image sensor 37 may include a laser rangefinder with a magnetic sensor, a camera with a laser range finder, or an ultrasound sensor.

Figure 4:
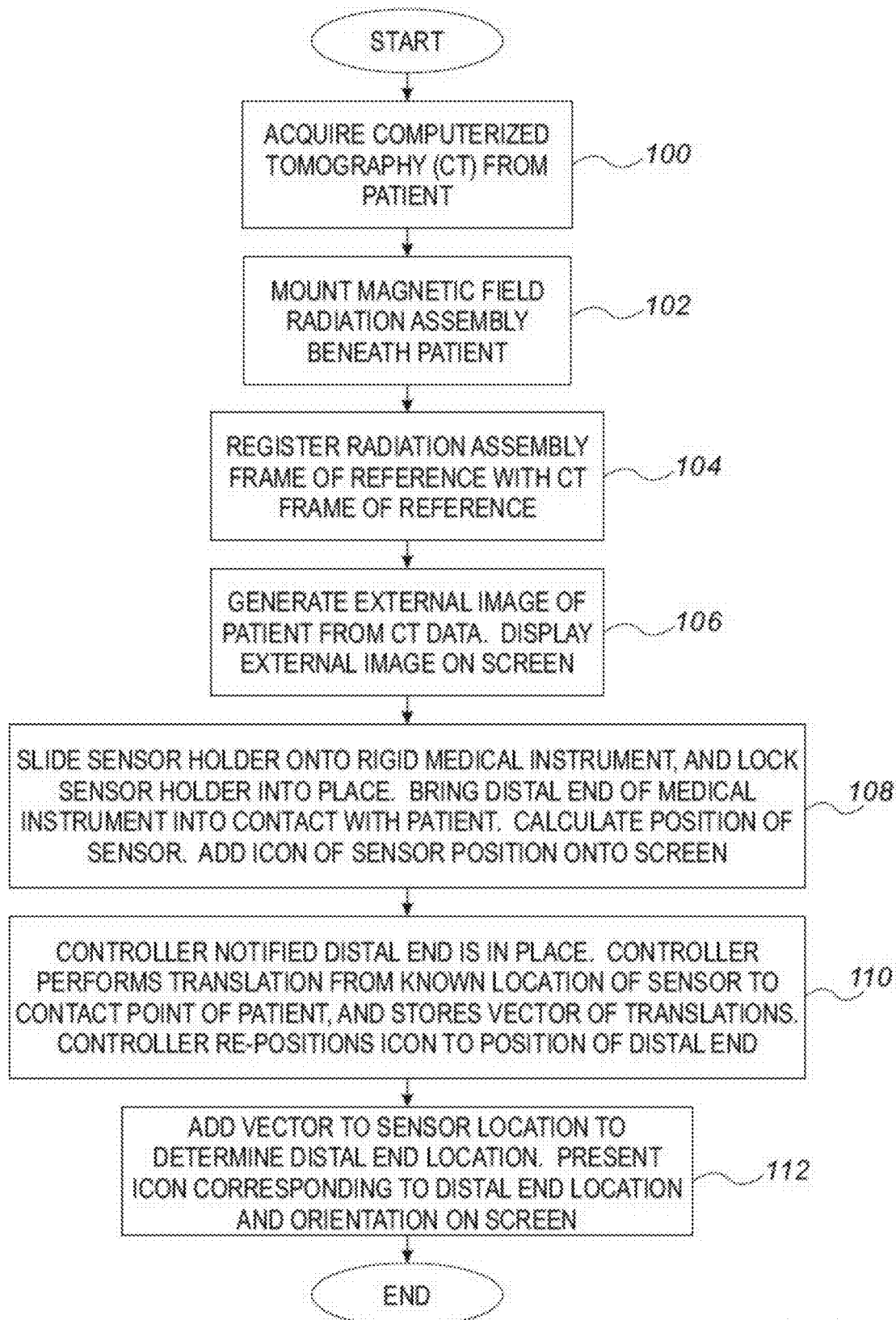
FIG. 4 is a flowchart and algorithm including exemplary steps that are implemented in the operation of the medical system of FIG. 1, according to an embodiment of the present invention.
Figure 5:
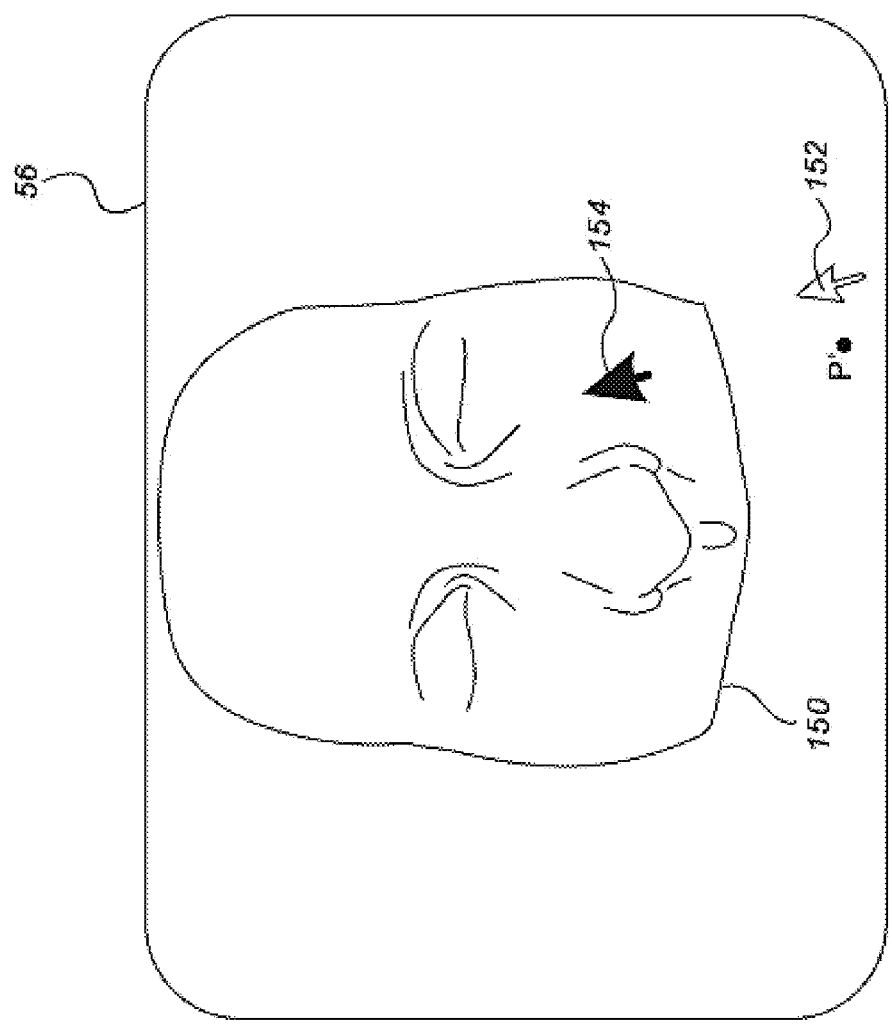
FIG. 5 is a schematic illustration of a screen used during implementation of the flowchart and algorithm, according to an embodiment of the present invention.

FIG. 4 is a flowchart including exemplary steps that are implemented in the operation of the medical system 20, and FIG. 5 is a schematic illustration of the display screen 56 during implementation of the flowchart, according to an embodiment of the present invention. The steps of the flowchart are also illustrated by FIGS. 1, 2, 3A, 3B, and 3C.

In an initial step 100, the head of patient 22 is scanned by computerized tomography (CT), herein by way of example assumed to be fluoroscopic CT, and the CT data from the scan is acquired by controller 38. The CT scan of patient 22 may be performed independently of the implementation of the remaining steps of the flowchart, which correspond to the medical procedure. Typically, step 100 may be performed a number of days before the following steps of the medical procedure. In some embodiments, any other suitable medical scan may supplement or replace the CT scan.

In a first procedure step 102, the radiation assembly 24 is mounted beneath or behind the head of the patient 22. Radiators 26 are then operated, and in a registration step 104, a frame of reference of the radiators 26 is registered with the frame of reference of the subject's head. The registration is typically performed by any means known in the art, e.g., by placing a magnetic field sensor coil such as the position sensor 36, or a grouping of such coils, in one or more known locations and orientations with respect to the external features of the patient 22 as well as with the magnetic field radiation assembly 24 holding the radiators 26. Generally, in this step, the controller 38 is configured to register the CT data (or other medical scan) with respect to at least one given location of the body-part (e.g., the external features of the patient 22).

In an initial display step 106, controller 38 generates a representation 150, also referred to herein as image 150, of external features of the patient 22, using the CT data received in step 100. The CT data is in the form of voxels with Hounsfield units (HU), and the image 150 of the external features of patient 22 is generated from voxel values and their HU values. The image 150 is typically a grayscale image. The values of the grayscales, from black to white, may be correlated with the Hounsfield unit (HU) of the corresponding voxels.

The HU values are radiodensity values and as is known in the art, apart from the values for air and water, which by definition are respectively −1000 and 0, the value of the Hounsfield unit of any other substance or species, such as dense bone, is dependent, inter alia, on the spectrum of the irradiating X-rays used to produce the CT scans referred to herein. In turn, the spectrum of the X-rays depends on a number of factors, including the potential in kV applied to the X-ray generator, as well as the composition of the anode of the generator. For clarity in the present disclosure, the values of Hounsfield units for a particular substance or species are assumed to be as given in Table I below.

TABLE I

| Species/Substance | Hounsfield Unit |
|---|---|
| Air | −1000 |
| Soft Tissue | −300 to −100 |
| Fat | −50 |
| Water | 0 |
| Blood | +30 to +45 |
| Dense Bone | +3000 |

However, the numerical values of HUs for particular species (other than air and water) as given in Table I are to be understood as being purely illustrative, and those having ordinary skill in the art will be able to modify these illustrative values, without undue experimentation, according to the species and the X-ray machine used to generate the CT images referred to herein. Typically, a translation between HU values and grayscale values is encoded into a DICOM (Digital Imaging and Communications in Medicine) file that is the CT scan output from a given CT machine.

The controller 38 displays image 150 on the display screen 56, and FIG. 5 schematically illustrates the image 150 as displayed on the display screen 56.

The HU values also provide an indication of the different tissue types (e.g., bone, soft tissue, fat, blood) at different locations in the CT images. Registration of the CT scan with the medical system 20 may enable an anatomical feature next to the medical instrument 28 to be identified based on the HU values of the voxels at the location of the medical instrument 28. For example, soft tissue may be identified as being at the distal end 34 of the medical instrument 28 based on the HU values in the CT scan at the location of the distal end 34. Alternatively, dense bone may be identified in the CT scan based on the HU values near the distal end 34. Other anatomical features may be identified either automatically (using image analysis techniques) or manually (by a trained operator or radiologist) from analysis of the CT scan. The identified anatomical features may then be registered with the medical system 20 for use during a medical procedure. Therefore, different anatomical features may be identified as being close to the distal end 34, or another location of the medical instrument 28, when the medical instrument 28 is inserted in the body-part. The medical instrument 28 may be controlled to avoid applying excessive force to anatomical features based on a sensitivity of the anatomical features. For example, the optic nerve may be identified in the CT scan automatically, or by a radiologist, and then registered with the medical system 20 for use during a medical procedure. The medical instrument 28 may be controlled to avoid applying excessive force to the optic nerve when the medical instrument 28 is at the location of the optic nerve. These features are described in more detail with reference to FIG. 6.

In an operation step 108, the physician slides hole 68 of the sensor holder 64 onto the rigid cylinder 60 of the medical instrument 28, and the physician 54 then uses setscrew 72 to lock the sensor holder in place, near proximal end 52 of the medical instrument 28. Once the holder 64 is locked in place, the robotic arm 40 is set into loose mode that allows manual movement of the robotic arm 40 by the physician 54. The physician 54 brings the distal end 34 of the medical instrument 28 into contact with a selected region of the external features of the patient 22, for example a region at the side of the patient's nose.

The positioning of the distal end 34 brings the sensor holder 64 and its encapsulated position sensor 32 into the region 30, so that the controller 38 is able to calculate the location and orientation of the position sensor 32. Once the controller 38 has performed this calculation, it typically introduces an icon 152, representative of sensor direction 70, onto the display screen 56, in proximity to image 150. The icon 152 is located and orientated on the display screen 56 in accordance with the location and orientation of the position sensor 32, determined from the sensor signals, within the common frame of reference of the image 150 and the magnetic field radiators 26.

By virtue of the fact that the physician 54 is manipulating the medical instrument 28, the physician 54 is aware of the actual location and orientation of the position sensor 32. Comparison of the location and orientation of icon 152 with the actual location and orientation of position sensor 32 provides confirmation to the physician 54 of the correct operation of the medical system 20.

In a calibration step 110, the physician 54 notifies the controller 38 that the distal end 34 of the medical instrument 28 is in contact with an external feature of the patient 22, typically by using controls 51. On receipt of the notification, the controller 38 performs two translations on the known location of the position sensor 32. A first translation corresponds to vector V (A, θ), (FIG. 3C) so that the controller 38 translates the location of the position sensor 32 by a value A along a direction defined by θ to a point P on axis 62 (FIG. 3A). A point P', corresponding to point P, is drawn in FIG. 5, to illustrate the termination of the first translation. Typically, point P' is not drawn on screen 56.

From point P, the controller 38 performs a second translation, in a direction corresponding to direction φ. Since the axes 69 and 62 are coincident, the second translation is in a direction corresponding to translating along the axis 62. The controller 38 uses the data for the image 150 to determine the actual length of the second translation, by determining from the image data where point P, moving in direction along axis 69, meets an external surface of patient 22. The meeting with the external surface occurs when there is at least a predetermined change in radiodensity as measured in the image, e.g., a change in the value of the Hounsfield units of the image data. Suitable values for the change are 200-500 Hounsfield units. The meeting is assumed to be at a point Q on axis 62. Point Q is at a distance B, now known, from point P, and the second translation thus corresponds to a vector (B, φ), herein also termed vector W, and illustrated in FIG. 3C.

It will be understood that even though the calculation of the position of point Q uses CT image data, since the image 150 is registered with the actual external features of patient 22, point Q corresponds with an actual external point of the patient 22.

At the conclusion of the calibration step, the controller 38 deletes icon 152 from screen 56, and positions an icon 154 at a position on the image 150 corresponding to point Q. Comparison of the location and orientation of the icon 154 with the actual location and orientation of the distal end 34 provides confirmation to the physician 54 of the correct completion of the calibration step.

The sum of the two translations, V+W, of the calibration step is a vector that is stored by the controller 38.

In a continuing tracking step 112, the controller 38 adds the vector stored in step 110 to the location of the position sensor 32 in order to determine the location of distal end 34. The orientation of the distal end 34 corresponds to direction φ, which is also determined by the controller 38 in tracking the position sensor 32. Thus, the controller 38 is able to calculate the location and orientation of the distal end 34 by computing the location and orientation of the position sensor 32. The controller 38 may position an icon corresponding to the location and orientation of the distal end 34 on the display screen 56. In some embodiments, if the distal end 34 is within patient 22, the external features of image 150 that may obscure the icon are rendered at least partially transparent. The position of the distal end 34 with respect to anatomic features of the patient 22 may be derived based on the calculated position of the distal end 34 with respect to coordinates on the registered image. In the above manner the distal end 34 of the medical instrument 28 may be guided into the body-part of the patient 22 to a desired location by observation of the movement of the icon in the captured CT or other images.

In some embodiments, the distal end 34 of the medical instrument 28 may be guided in to the body-part automatically by the robotic arm 40 based on a suitable path-finding algorithm. An example algorithm is described with reference to US Published Patent Application No. 2017/0056112A1 of Gliner, et al. which is herein incorporated by reference.

Figure 6:
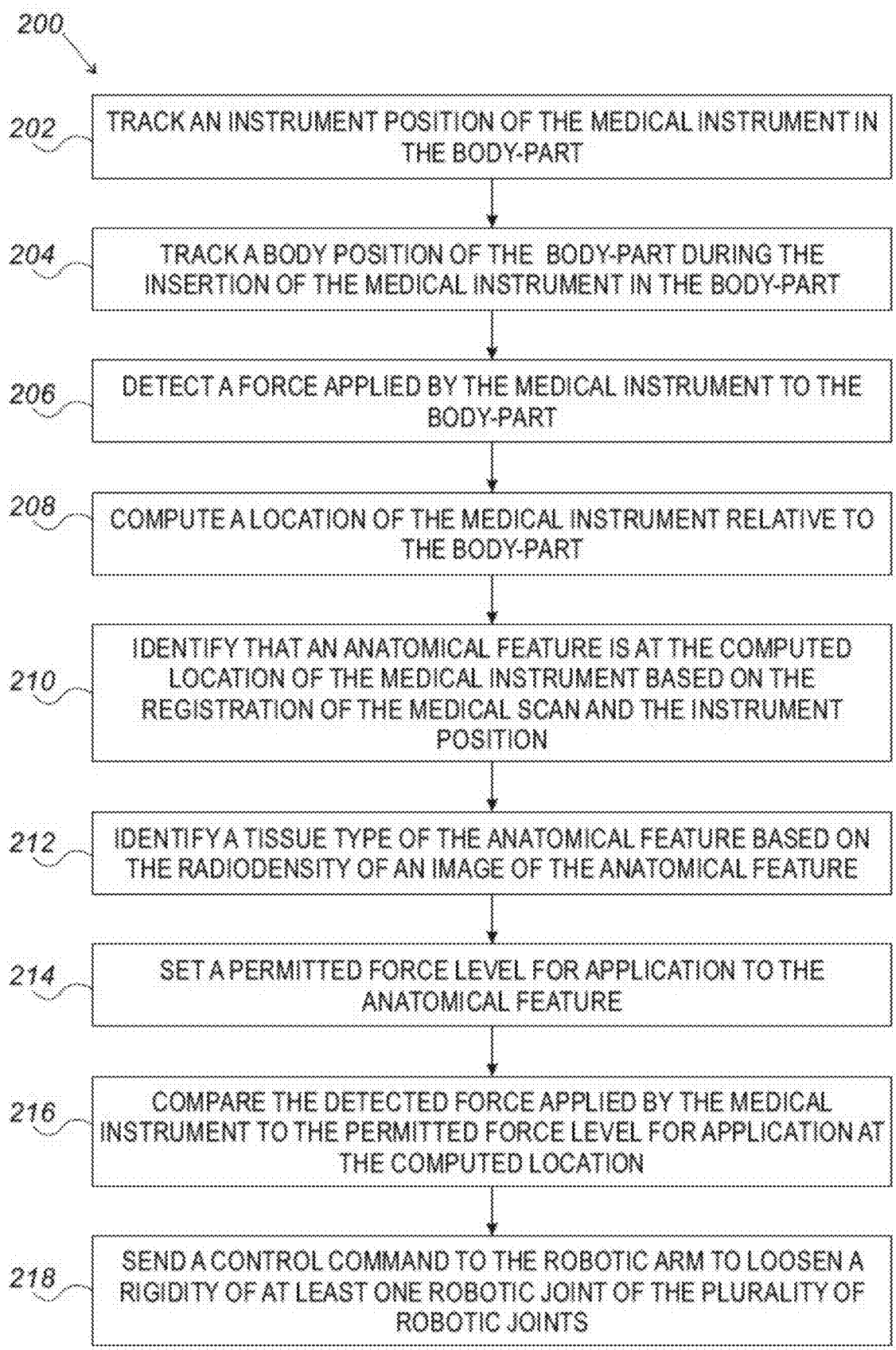
FIG. 6 is a flowchart and algorithm including exemplary steps in a method for use in the medical system of FIG. 1.

Reference is now made to FIG. 6, which is a flowchart 200 including exemplary steps in a method for use in the medical system 20 of FIG. 1. Reference is also made to FIG. 1.

As described above with reference to FIG. 4, The HU values of the CT scan provide an indication of the different tissue types (e.g., bone, soft tissue, fat, blood) or other substances (e.g., water or air) at different locations in the CT images. Registration of the CT scan with the medical system 20 may enable an anatomical feature next to the medical instrument 28 to be identified based on the HU values of the voxels at the location of the medical instrument 28. For example, soft tissue may be identified as being at the distal end 34 of the medical instrument 28 based on the HU values in the CT scan at the location of the distal end 34. Alternatively, dense bone may be identified in the CT scan based on the HU values near the distal end 34. Other anatomical features may be identified either automatically (using image analysis techniques) or manually (by a trained operator or radiologist) from analysis of the CT scan. The identified anatomical features may then be registered with the medical system 20 for use during a medical procedure. For example, the optic nerve may be identified in the CT scan automatically or by a radiologist and then registered with the medical system 20. The medical instrument 28 may be controlled to avoid applying excessive force to the optic nerve when the medical instrument 28 is at the location of the optic nerve.

The position sensor 32 is configured to track (block 202) an instrument position of the medical instrument 28 in the body-part. The position sensor 36 is configured to track (block 204) a body position of the body-part during the insertion of the medical instrument 28 in the body-part. The force sensor 35 (FIG. 3A) is configured to detect (block 206) a force applied by the medical instrument 28 to the body-part.

The controller 38 is configured to compute (block 208), responsively to the instrument position and the body position, a location of the medical instrument 28 relative to the body-part.

The controller 38 is configured to identify (block 210) that an anatomical feature is at the computed location of the medical instrument 28 based on the registration of the medical scan and the instrument position. For example, the controller 38 identifies a location in the CT scan corresponding with the computed location of the medical instrument 28. The location of the CT scan may include an anatomical feature. The anatomical feature may be a tissue type which is identified in step 212 below. Additionally, or alternatively, the anatomical feature may be an organ or nerve or other feature that was identified in the CT scan automatically (e.g., using image analysis) or by a radiologist and then registered with the medical system 20 prior to the medical procedure.

The controller 38 is configured to identify (block 212) a tissue type (e.g., bone, soft tissue, blood, fat) of the anatomical feature based on the radiodensity (e.g., HU value) of the image of the anatomical feature. Additionally, or alternatively, the controller 38 is configured to identify (block 212) an identification of the anatomical feature (e.g., the optic nerve or brain) based on an identification of the anatomical feature that was registered with the medical system 20 prior to the medical procedure.

The controller 38 is configured to set (block 214) a permitted force level for application to the anatomical feature. In some embodiments, the controller 38 is configured to set the permitted force level for application to the anatomical feature based on a known or estimated sensitivity and/or importance of the anatomical feature. For example, the optic nerve may be more important than another nerve. In some embodiments, the controller 38 is configured to set the permitted force level for application to the anatomical feature based on a sensitivity and/or importance of the tissue type of the anatomical feature. For example, soft tissue is more sensitive than hard bone. In some embodiments, the controller 38 is configured to set the permitted force level for application to the anatomical feature based on the radiodensity (e.g., HU value) of the image of the anatomical feature. By way of example only, the permitted force level may be set to 2 gram-force (gmf) for tissue surrounding the eye orbit, less than 1 gmf for the optic nerve, and 30 gmf for nasal bone, where 1 gmf is equivalent to the weight of 1 gram of mass at standard gravity.

The controller 38 is configured to compare (block 216) the detected force applied by the medical instrument 28 to a permitted force level for application to the anatomical feature at the computed location. If the medical instrument 28 includes multiple force sensors 35, the reading from the force sensors 35 may be averaged. Additionally, or alternatively, the readings from the different force sensors 35 may be processed individually by the controller 38 wherein the controller 38 compares the detected force at the location of each respective force sensor 35 with the permitted force level for the anatomical feature adjacent to each of the respective force sensors 35.

The controller 38 is configured to send (block 218) a control command to, or cut power of, the robotic arm 40 to loosen a rigidity of at least one robotic joint of the plurality of robotic joints of the robotic arm 40 in response to the detected force applied by the medical instrument 28 at the computed location being greater than the permitted force level. The loose mode may even lead to the robotic arm 40 dropping the medical instrument 28, but this is acceptable compared to the risk of trauma if there is still feedback to the actuators of the robotic arm 40. In some embodiments, the controller 38 is configured to send a control command to the robotic arm 40 to drop the medical instrument 28 in response to the detected force applied by the medical instrument 28 at the computed location being greater than the permitted force level.

The above method described with reference to FIG. 6 may be suitably adapted to output a warning to the display screen 56 (FIG. 1) when the medical instrument 28 is too close to a sensitive tissue. The sensitive tissues may be predefined by the physician 54 or a system administrator. The definition of what is considered too close to sensitive tissue may also be predefined by the physician 54 or a system administrator, and the distance may be different for different sensitive tissues.

Figure 7:
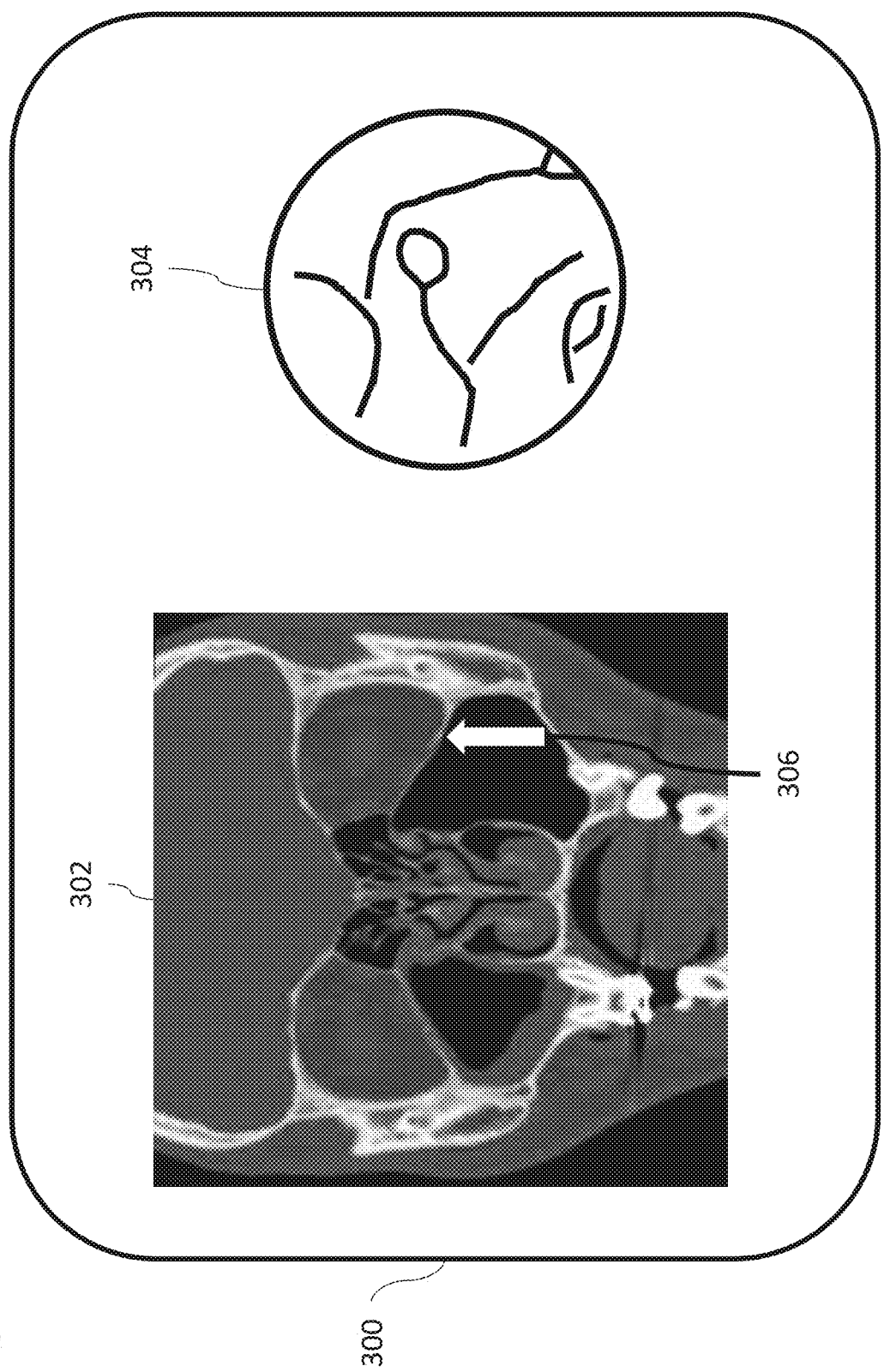
FIG. 7 is a schematic view of a user interface screen including an image of a medical scan and an image captured by an image sensor.

Reference is now made to FIG. 7, which is a schematic view of a user interface screen 300 including an image 302 of a segmented medical scan and an image 304 captured by the image sensor 37 of the medical instrument 28 for use in the medical system 20 of FIG. 1. The medical scan may be a CT scan or any other suitable scan, for example, but not limited to an MRI scan.

The image 304 captured by the medical instrument 28 (FIG. 1) and the image 302 of the segmented medical scan are displayed together on the display screen 56 (FIG. 1). The image 302 of the segmented medical scan indicates different initial tissues-types (e.g., bone, soft-tissue, cartilage, blood) or matter types (e.g., water or air) using a color-scheme (e.g., grayscale). For example, air may be black or close to black and bone may be white or off-white. A representation 306 of the medical instrument 28 (e.g., using an arrow or a schematic graphic of the medical instrument) is superimposed over the image 302 of the segmented medical scan to show the current position of the medical instrument 28.

Figure 8:
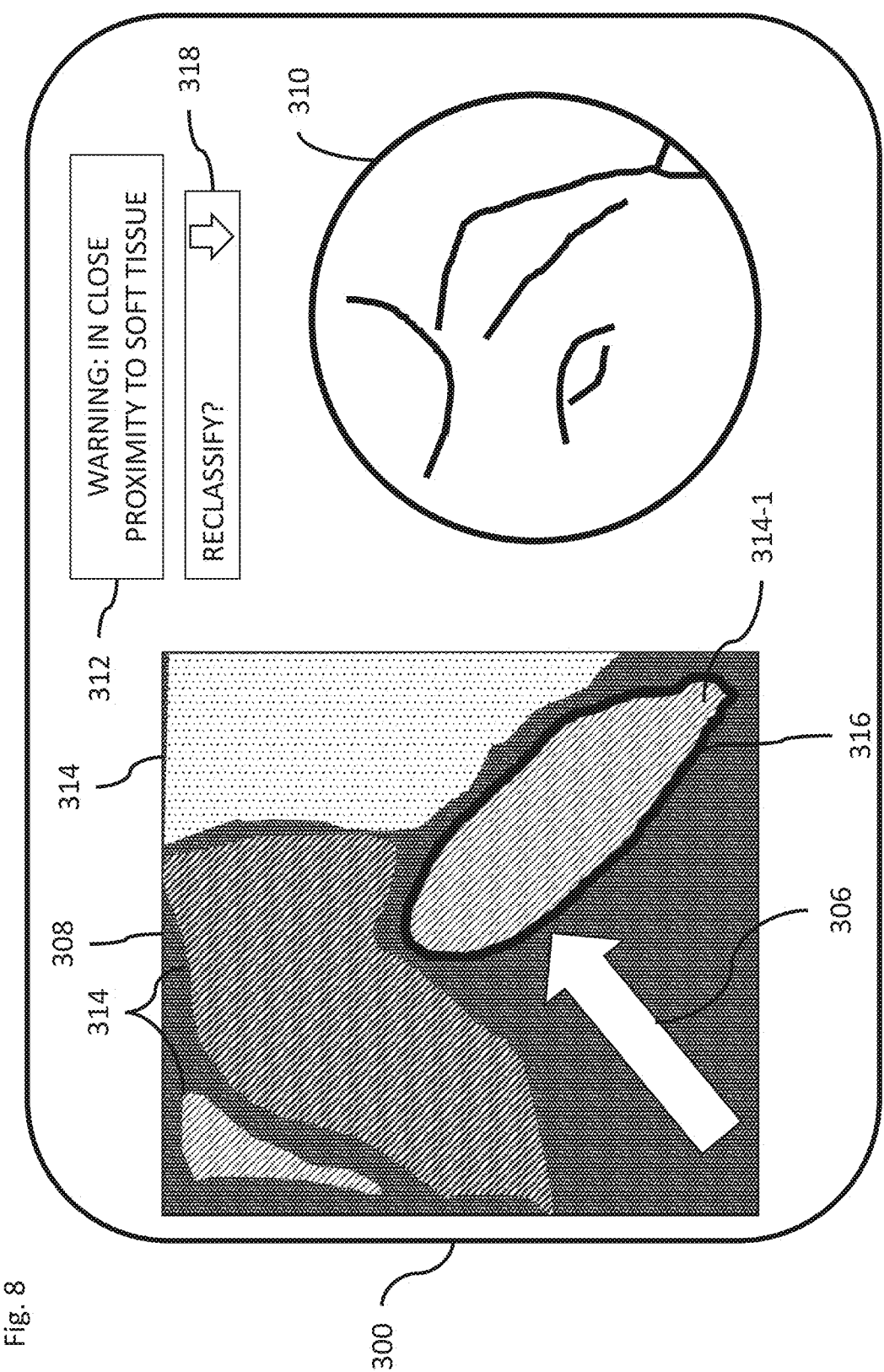
FIG. 8 is a schematic view of the user interface screen of FIG. 7 showing an image of another part of the medical scan, a different image captured by the image sensor, and a warning.

Reference is now made to FIG. 8, which is a schematic view of the user interface screen 300 of FIG. 7 showing an image 308 of another part of the medical scan, a different image 310 captured by the image sensor 37 (FIG. 1), and a warning 312. The image 308 shows different tissues 314 having corresponding tissue-type indications. The tissue-type indications are distinguished based on the grayscale values used to fill the tissues 314 shown in the image 308. One of the tissues 314, a tissue 314-1, is emphasized using a border 316 to indicate that the tissue 314-1 corresponds to the tissue currently being captured by the image sensor 37 and displayed in the image 310. Additionally, or alternatively, the tissue 314-1 may be emphasized using an arrow, a change of format or any other suitable emphasizing method.

Based on the proximity of the medical instrument 28 (FIG. 1) to the tissue 314-1, as shown by the representation 306 on the image 308, and based on the tissue 314-1 being initially classified as sensitive tissue based on the tissue-type indication of the tissue 314-1 in the medical scan, the controller 38 may be configured to output the warning 312 on the user interface screen 300 that the medical instrument 28 is too close to the tissue 314-1 (e.g., the medical instrument 28 is too close to soft-tissue).

The proximity of the medical instrument 28 to the tissue 314-1 may be computed by the controller 38 based on the tracked position of the medical instrument 28 and the location of the various tissues 314 in the medical scan, which is registered with the coordinate frame of the medical instrument 28.

A comparison by the physician 54 (FIG. 1) of the tissue included in the image 310 with the tissue-type indication (e.g., grayscale value) of the emphasized tissue 314-1 included in the image 308 of the medical scan may reveal that the initial tissue-type indication of the emphasized tissue 314-1 is incorrect.

The user interface screen 300 includes a drop-down list 318 that may be used to correct the initial tissue-type indication of the tissue 314-1.

Figure 9:
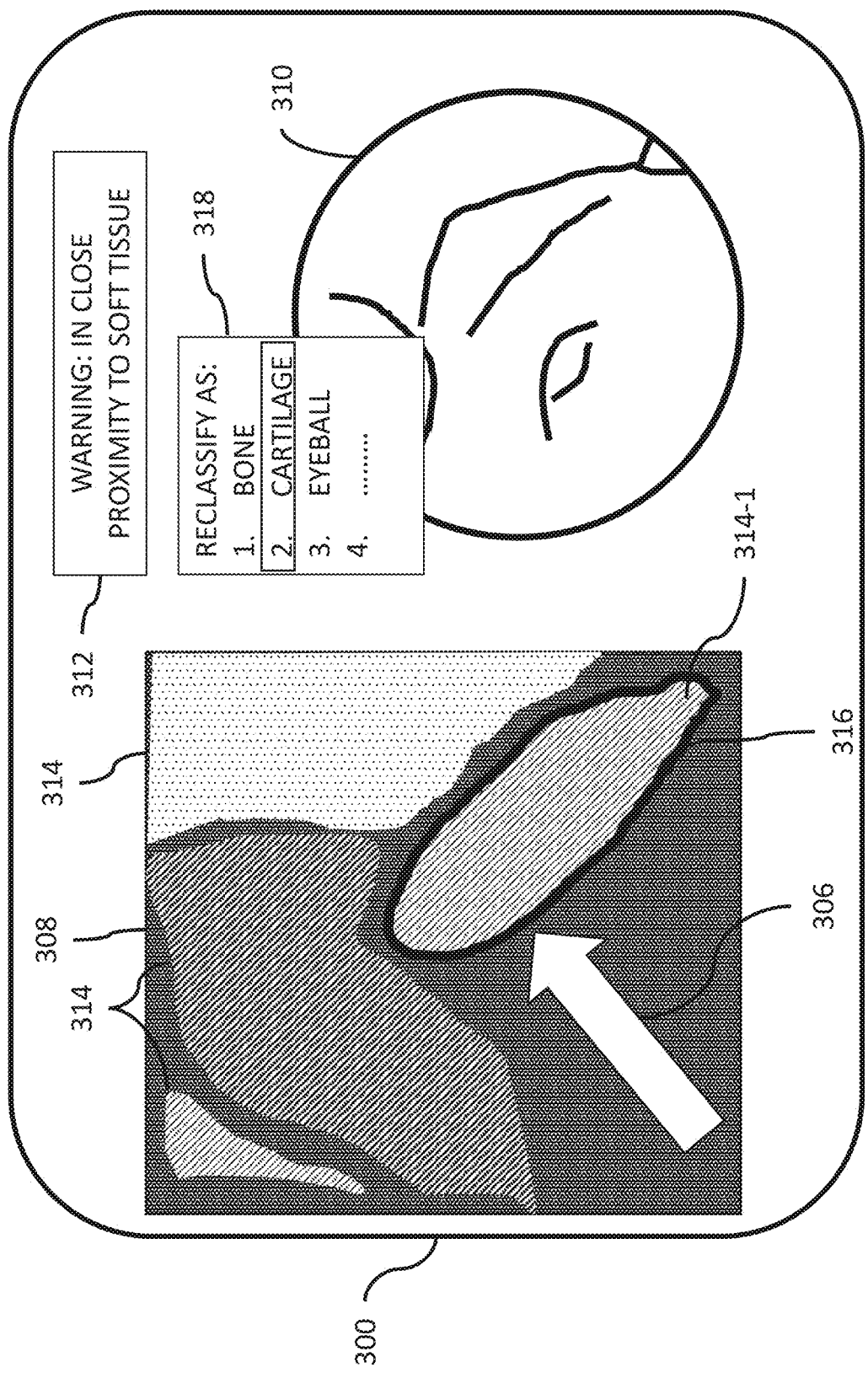
FIG. 9 is a schematic view of the user interface screen of FIG. 8 showing a reclassification drop-down list.

Reference is now made to FIG. 9, which is a schematic view of the user interface screen 300 of FIG. 8 showing the reclassification drop-down list 318. The physician 54 may then select the correct tissue-type from the drop-down list 318 or by entering a corrected grayscale value or Hounsfield unit value into a suitable input field. In the example of FIG. 9, the initial classification of the tissue 314-1 is changed from "soft tissue" to "cartilage".

Figure 10:
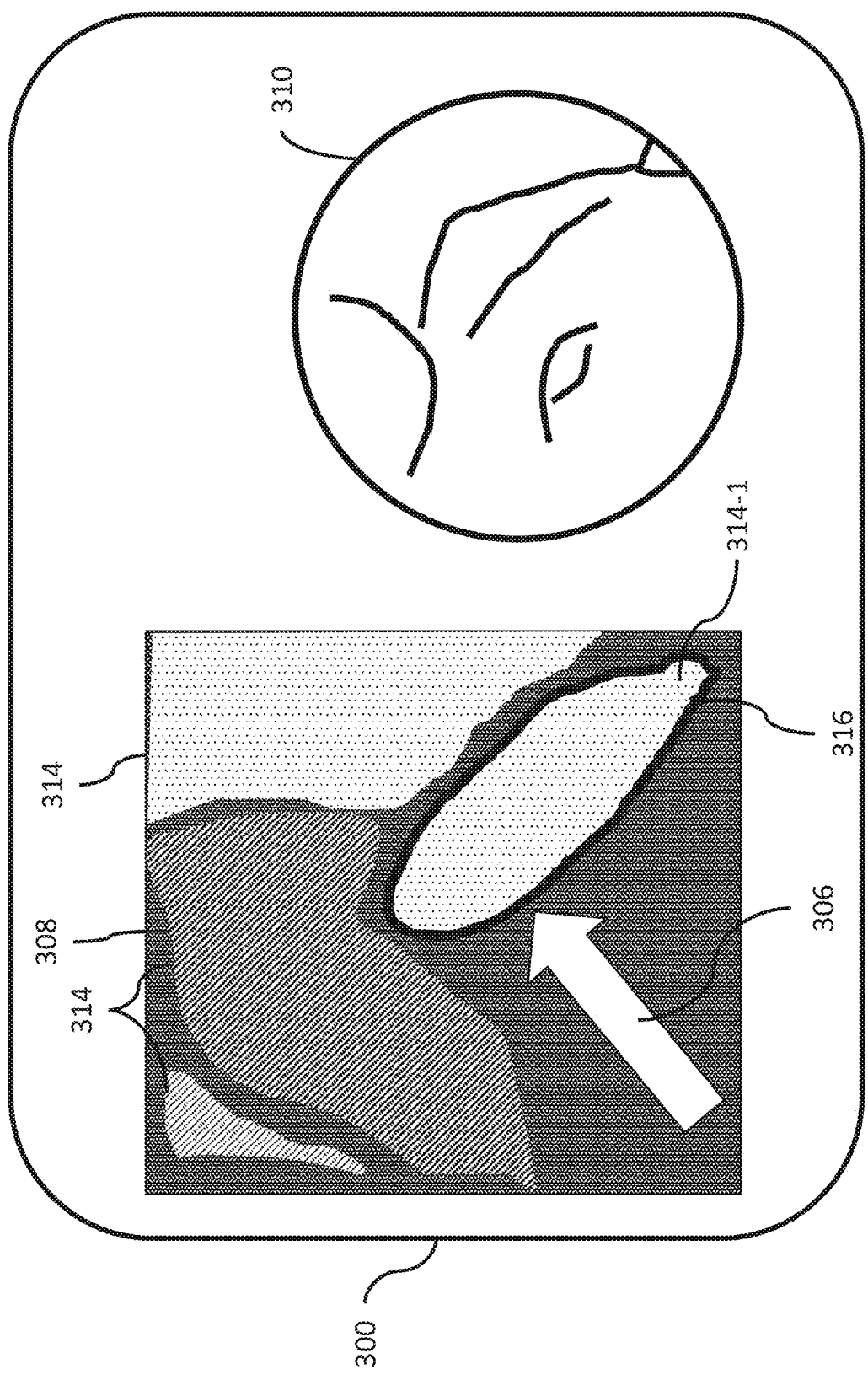
FIG. 10 is a schematic view of the user interface screen of FIG. 8 after reclassification of the tissue.

Reference is now made to FIG. 10, which is a schematic view of the user interface screen 300 of FIG. 8 after reclassification of the tissue 314-1. FIG. 10 shows that the grayscale value of the tissue 314-1 has been lightened to reflect the change from soft-tissue to cartilage. In addition to showing the change in the tissue-type indication of the tissue 314-1 in the image 308, the tissue-type indication of the tissue 314-1 is also updated in data of the medical scan.

Figure 12:
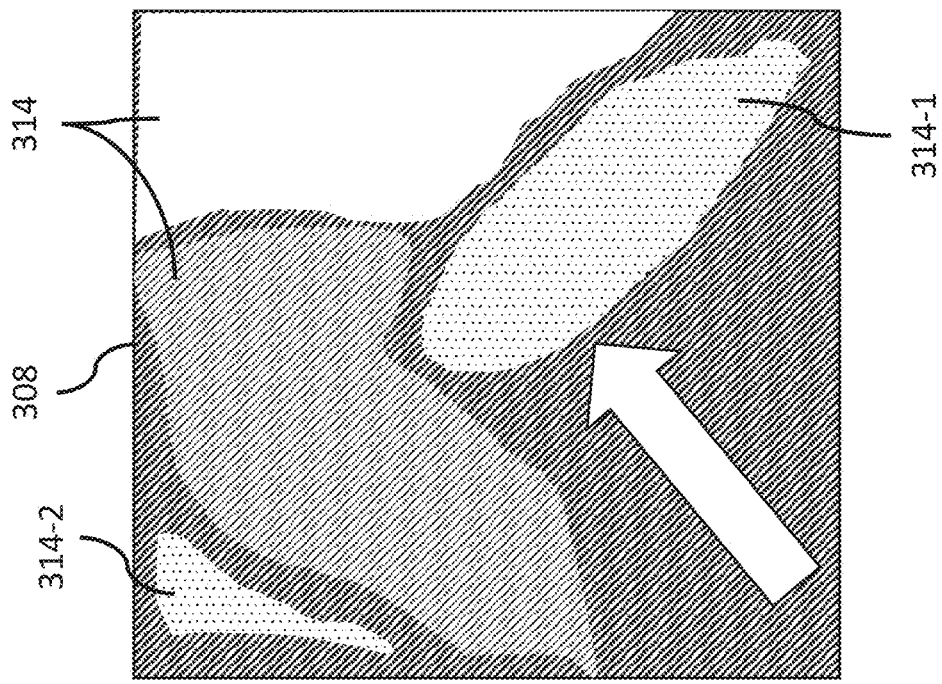
FIGS. 11 and 12 are schematic views of the image of the other parts of the medical scan of FIG. 8 after multi-tissue reclassification.
Figure 11:
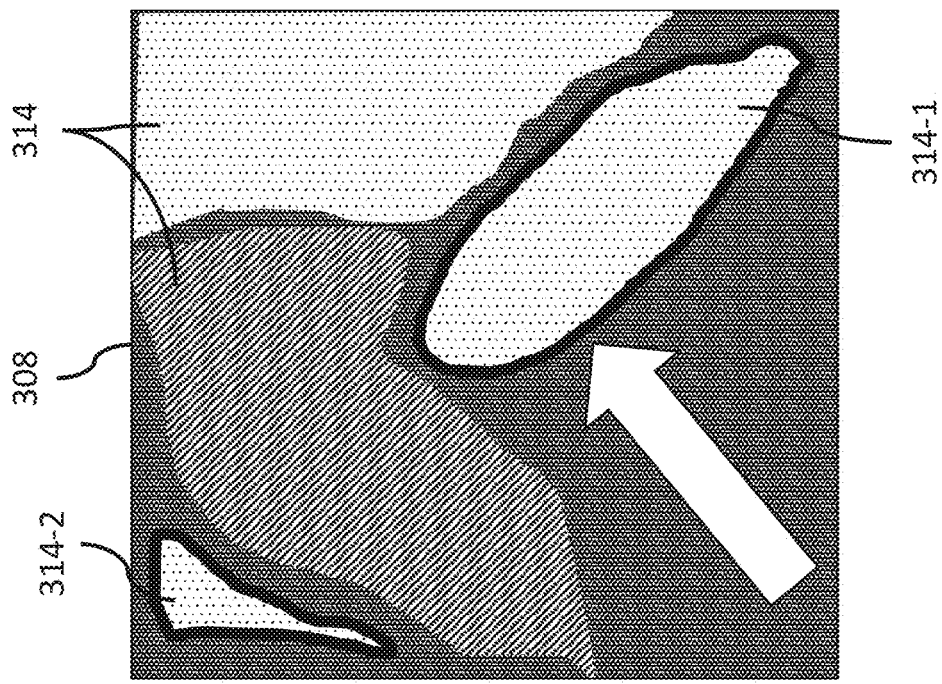

Reference is now made to FIGS. 11 and 12, which are schematic views of the image 308 of the other tissues of the medical scan of FIG. 8 after multi-tissue reclassification.

In some embodiments, the tissue-type indication may be updated for all tissues 314 having the same initial tissue-type indication as the tissue 314-1 as it may be assumed that the same error propagated itself throughout the medical scan. By way of example, if the Hounsfield unit value of the tissue 314-1 was initially 300 and is now modified to 600, the Hounsfield unit values of all the tissues 314 in the medical scan having an initial Hounsfield unit value of 300 are now modified to 600. FIG. 11 shows that a tissue 314-2, which had the same initial tissue-type indication as the tissue 314-1, has also been updated in the image 308 (and in the medical scan data) when the tissue-type indication of the tissue 314-1 was updated.

In some embodiments, all the initial tissue-type indications in the medical scan may be updated proportionally according to the proportional change in value (e.g., grayscale value or Hounsfield unit value) from the initial tissue-type indication to the modified tissue-type-indication of the tissue 314-1. By way of example, if the Hounsfield unit value of the tissue 314-1 was initially 300 and is now modified to 600 (i.e., it doubled) all the Hounsfield unit values of the tissues 314 in the medical scan are doubled. FIG. 12 shows that all the gray scale values of all the tissues 314 of the image 308 have been lightened.

Figure 13:
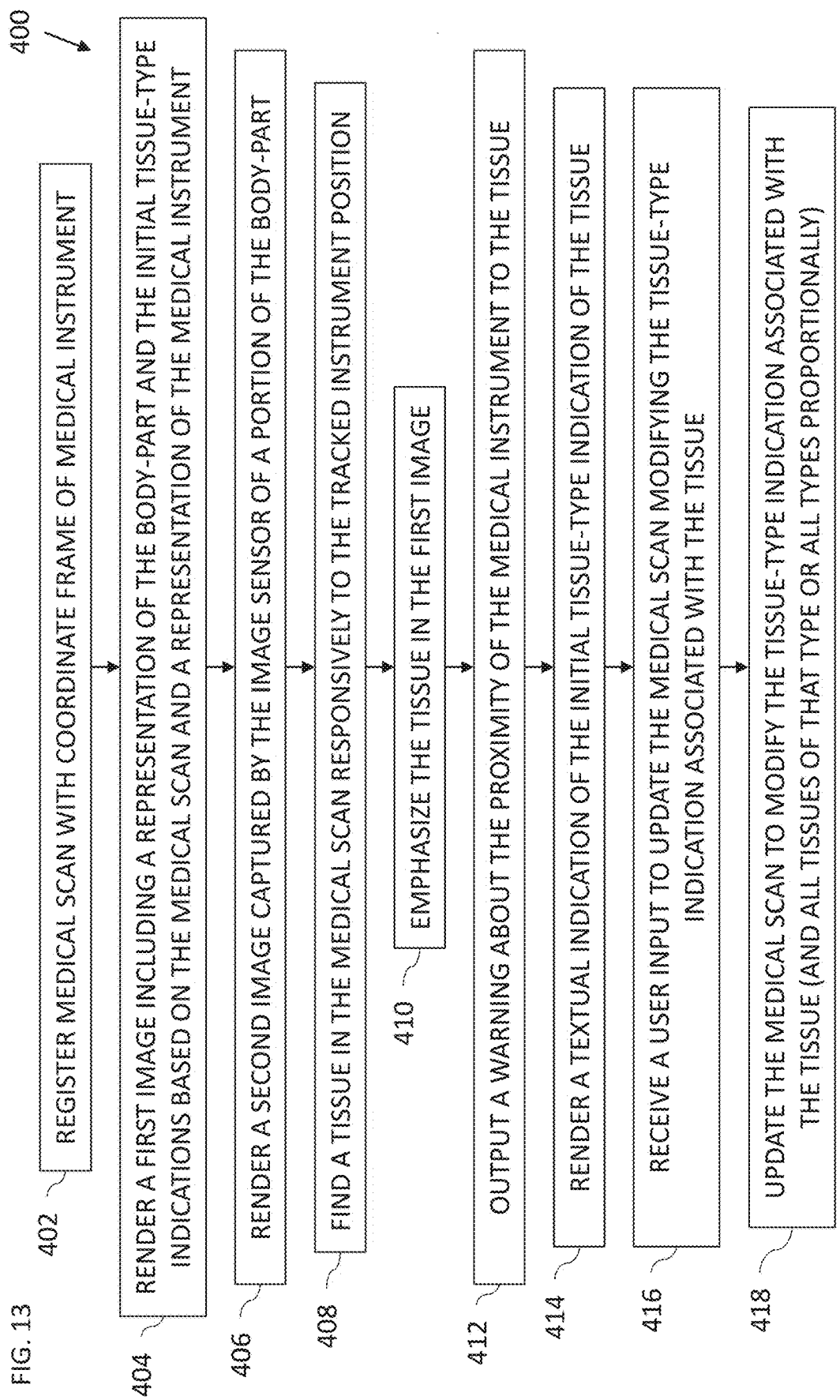
FIG. 13 is a flowchart including exemplary steps in a method of operation of the medical system of FIG. 1 according to an embodiment of the present invention.

Reference is now made to FIG. 13, which is a flowchart 400 including exemplary steps in a method of operation of the medical system 20 of FIG. 1 according to an embodiment of the present invention. Reference is also made to FIGS. 1 and 8.

The controller 38 is configured to register (block 402) the medical scan of the body-part with the coordinate frame of the medical instrument 28. Registration has been described in more detail with reference to FIGS. 4 and 5. The medical scan includes a plurality of initial tissue-type indications of the body-part. The initial tissue-type indications may be levels of radiodensity in the medical scan (e.g., Hounsfield unit values), or gray scale values, or any other suitable indication of tissue-type for example, but limited to, a tissue-type name, e.g., bone or soft-tissue.

The controller 38 is configured to render (block 404) to the display screen 56, the image 308 including: a representation of the body-part and the initial tissue-type indications based on the medical scan; and a representation 306 of the medical instrument 28 disposed at the tracked instrument position (tracked by the position sensor 32 or any other suitable sensor and/or tracking system) in the body-part.

The controller 38 is configured to render (block 406) to the display screen 56, the image 310 captured at the tracked instrument position by the image sensor 37 (FIG. 3A) of a portion of the body-part. The image 308 and the image 310 are typically displayed on the display screen 56 at the same time, for example, on the user interface screen 300.

The controller 38 is configured to find (block 408) the tissue 314-1 in the medical scan responsively to the tracked instrument position of the medical instrument 28 and the distance from the image sensor 37 to the tissue 314-1 based on the optical configuration or other known features of the image sensor 37. The medical instrument 28 may also include a rangefinder to determine the distance between the image sensor 37 and the tissue 314-1.

The controller 38 is configured to emphasize (block 410) the tissue 314-1 in the image 308, for example, using the border 316.

In some embodiments, the controller 38 is configured to output (block 412), to the display screen 56, the warning 312 about the proximity of the medical instrument 28 to the tissue 314-1 responsively to the tracked instrument position and the tissue 314-1 being initially classified in the medical scan according to the initial tissue-type indication (e.g., sensitive tissue) of the tissue 314-1.

In some embodiments, the controller 38 is configured to render (block 414) to the display screen 56, a textual indication (e.g., "Soft-tissue" or "Bone" etc.) of the initial tissue-type indication of the tissue 314-1. The step of block 414 may be performed in addition to, or instead of, the step of block 412.

In some embodiments, the operating controls 51 (FIG. 1) are configured to receive (block 416) a user input to update the medical scan modifying the tissue-type indication associated with the tissue 314-1 from the initial tissue-type indication of the tissue 314-1. The user input may be facilitated using the drop-down list 318 whereby the physician 54 selects a new tissue-type from the drop-down list 318. Alternatively, the physician 54 may enter (or select) a new grayscale value or Hounsfield unit value of the tissue 314-1. Hounsfield units are used herein by way of example only, any suitable radiodensity unit may be used.

In some embodiments, the comparison of the tissue included in the image 310 with the tissue-type indication (e.g., grayscale value) of the tissue 314-1 included in the medical scan may be performed in an automatic or semi-automatic fashion. The controller 38 may be configured to compare the tissue included in the image 310 with other tissue images in a library of tissue images to identify the tissue-type of the tissue in the image 310. Additionally, or alternatively, machine learning techniques may also be used by the controller 38 to identify the tissue-type of the tissue included in the image 310. The identified tissue-type may then be compared to the initial tissue-type indication of the tissue 314-1 included in the medical scan. If the identified tissue-type is different from the initial tissue-type indication, the controller 38 may automatically update the initial tissue-type indication to the identified tissue-type or the controller 38 may output a message to the display screen 56 informing the physician 54 that the tissue-type of tissue viewed in the image 310 is not the same as the initial tissue-type indication of the tissue 314-1 included in the medical scan. The physician 54 then has the option to approve or deny updating the initial tissue-type indication to the identified tissue-type.

Responsively to the comparison (manual, automatic or semi-automatic) between an appearance of the tissue in the image 310 of the portion of the body-part and an initial tissue-type indication of the tissue 314-1, the controller 38 is configured to update (block 418) the medical scan to modify the tissue-type indication associated with the tissue 314-1 (to the tissue-type indication selected by the physician 54 or the controller 38 or approved by the physician 54).

In some embodiments, the controller 38 is configured to update the medical scan to reclassify all tissues 314 of the body-part in the medical scan initially classified with the initial tissue-type indication of the tissue 314-1 to the modified tissue-type indication of the tissue 314-1. By way of example, if the Hounsfield unit value of the tissue 314-1 was initially 300 and is now modified to 600, the Hounsfield unit values of all the tissues 314 in the medical scan having an initial Hounsfield unit value of 300 are now modified to 600.

In some embodiments, the controller 38 is configured to update proportionally all the levels of radiodensity in the medical scan responsively to a proportional change between the level of radiodensity of the initial tissue-type indication of the tissue 314-1 and the level of radiodensity of the modified tissue-type indication of the tissue 314-1. By way of example, if the Hounsfield unit value of the tissue 314-1 was initially 300 and is now modified to 600 (i.e., it doubled) all the Hounsfield unit values of the tissues 314 in the medical scan are doubled. In other embodiments, the controller 38 is configured to update all the levels of radiodensity in the medical scan responsively to a proportional change confirmed by at least two tissue-type indication updates from different ones of the plurality of initial tissue-type indications. For example, if the Hounsfield unit value of the tissue 314-1 was initially 300 and is now modified to 600 (i.e., it doubled) and the Hounsfield unit value of another tissue 314 was initially 400 and is now modified to 800 (i.e., it doubled) all the Hounsfield units of the tissues 314 in the medical scan are doubled based on the confirmation of the proportionality (e.g., doubling) of the first update.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical scan correction system comprising:
a medical instrument having a distal end and an image sensor disposed at the distal end, and configured to be inserted into a body-part of a living subject;
a position sensor configured to track an instrument position of the medical instrument in the body-part;
a display; and
a controller configured to:
register a medical scan of the body-part with a coordinate frame of the medical instrument, the medical scan including a plurality of initial tissue-type indications of the body-part;
render to the display, a first image including: a representation of the body-part and the plurality of initial tissue-type indications based on the medical scan; and a representation of the medical instrument disposed at the tracked instrument position in the body-part;
render to the display, a second image captured at the tracked instrument position by the image sensor of a portion of the body-part; and
responsively to a comparison between an appearance of a tissue in the second image of the portion of the body-part and an initial tissue-type indication of the tissue, update the medical scan to modify the tissue-type indication associated with the tissue.

2. The system according to claim 1, further comprising operating controls configured to receive a user input to update the medical scan modifying the tissue-type indication associated with the tissue from the initial tissue-type indication of the tissue.

3. The system according to claim 1, wherein the controller is configured to find the tissue in the medical scan responsively to the tracked instrument position.

4. The system according to claim 1, wherein the controller is configured to render to the display, a textual indication of the initial tissue-type indication of the tissue.

5. The system according to claim 1, wherein the controller is configured to emphasize the tissue in the first image.

6. The system according to claim 1, wherein the plurality of initial tissue-type indications are levels of radiodensity in the medical scan.

7. The system according to claim 1, wherein the controller is configured to update the medical scan to reclassify all tissues of the body-part in the medical scan being initially classified with the initial tissue-type indication of the tissue to the modified tissue-type indication of the tissue.

8. The system according to claim 7, wherein the plurality of initial tissue-type indications are levels of radiodensity in the medical scan.

9. The system according to claim 8, wherein the controller is configured to update proportionally all the levels of radiodensity in the medical scan responsively to a proportional change between the level of radiodensity of the initial tissue-type indication of the tissue and the level of radiodensity of the modified tissue-type indication of the tissue.

10. The system according to claim 8, wherein the controller is configured to update all the levels of radiodensity in the medical scan responsively to a proportional change confirmed by at least two tissue-type indication updates from different ones of the plurality of initial tissue-type indications.

11. The system according to claim 1, wherein the controller is configured to output a warning about the proximity of the medical instrument to the tissue responsively to the tracked instrument position and the tissue being initially classified in the medical scan according to the initial tissue-type indication of the tissue.

12. A medical scan correction method, comprising:
tracking an instrument position of a medical instrument in a body-part of a living subject, the medical instrument having a distal end and an image sensor disposed at the distal end;
registering a medical scan of the body-part with a coordinate frame of the medical instrument, the medical scan including a plurality of initial tissue-type indications of the body-part;
rendering to a display, a first image including: a representation of the body-part and the plurality of initial tissue-type indications based on the medical scan; and a representation of the medical instrument disposed at the tracked instrument position in the body-part;
rendering to the display, a second image captured at the tracked instrument position by the image sensor of a portion of the body-part; and
responsively to a comparison between an appearance of a tissue in the second image of the portion of the body-part and an initial tissue-type indication of the tissue, updating the medical scan to modify the tissue-type indication associated with the tissue.

13. The method according to claim 12, further comprising receiving a user input to update the medical scan modifying the tissue-type indication associated with the tissue from the initial tissue-type indication of the tissue.

14. The method according to claim 12, further comprising finding the tissue in the medical scan responsively to the tracked instrument position.

15. The method according to claim 12, further comprising rendering to the display, a textual indication of the initial tissue-type indication of the tissue.

16. The method according to claim 12, further comprising emphasizing the tissue in the first image.

17. The method according to claim 12, wherein the plurality of initial tissue-type indications are levels of radiodensity in the medical scan.

18. The method according to claim 12, further comprising updating the medical scan to reclassify all tissues of the body-part in the medical scan being initially classified with the initial tissue-type indication of the tissue to the modified tissue-type indication of the tissue.

19. The method according to claim 18, wherein the plurality of initial tissue-type indications are levels of radiodensity in the medical scan.

20. The method according to claim 19, further comprising updating proportionally all the levels of radiodensity in the medical scan responsively to a proportional change between the level of radiodensity of the initial tissue-type indication of the tissue and the level of radiodensity of the modified tissue-type indication of the tissue.

21. The method according to claim 19, further comprising updating all the levels of radiodensity in the medical scan responsively to a proportional change confirmed by at least two tissue-type indication updates from different ones of the plurality of initial tissue-type indications.

22. The method according to claim 12, further comprising outputting a warning about the proximity of the medical instrument to the tissue responsively to the tracked instrument position and the tissue being initially classified in the medical scan according to the initial tissue-type indication of the tissue.

23. A software product, comprising a non-transient computer-readable medium in which program instructions are stored, which instructions, when read by a central processing unit (CPU), cause the CPU to:
- register a medical scan of a body-part of a living subject with a coordinate frame of a medical instrument configured to be inserted into the body-part, the medical scan including a plurality of initial tissue-type indications of the body-part;
- render to a display, a first image including: a representation of the body-part and the plurality of initial tissue-type indications based on the medical scan; and a representation of the medical instrument disposed at a tracked instrument position of the medical instrument in the body-part;
- render to the display, a second image of a portion of the body-part captured at the tracked instrument position by an image sensor of the medical instrument; and
- responsively to a comparison between an appearance of a tissue in the second image of the portion of the body-part and an initial tissue-type indication of the tissue, update the medical scan to modify the tissue-type indication associated with the tissue.

* * * * *